(12) United States Patent
Orlovski et al.

(10) Patent No.: US 6,465,677 B1
(45) Date of Patent: Oct. 15, 2002

(54) METHOD FOR THE PREPARATION OF N-NEOHEXYL-α-ASPARTYL-L-PHENYLALANINE METHYL ESTER FROM IMIDAZOLIDIN-4-ONE INTERMEDIATES

(75) Inventors: Vladislav Orlovski, Buffalo Grove; Indra Prakash, Hoffman Estates; Mike G. Scaros, Arlington Heights; Christine M. V. Moore, Mount Prospect, all of IL (US)

(73) Assignee: The NutraSweet Company, Chicago, IL (US)

( * ) Notice: Subject to any disclaimer, the term of this patent is extended or adjusted under 35 U.S.C. 154(b) by 0 days.

(21) Appl. No.: 09/441,512

(22) Filed: Nov. 17, 1999

Related U.S. Application Data

(60) Provisional application No. 60/109,132, filed on Nov. 19, 1998.

(51) Int. Cl.[7] ..................... C07C 229/00; C07D 233/14

(52) U.S. Cl. .......................... 560/41; 560/40; 548/334.1

(58) Field of Search ....................... 560/40, 41

(56) References Cited

U.S. PATENT DOCUMENTS

| 5,480,668 A | 1/1996 | Nofre et al. ................. 426/548 |
| 5,510,508 A | 4/1996 | Claude et al. ................. 560/41 |
| 5,728,862 A | 3/1998 | Prakash ....................... 560/40 |

FOREIGN PATENT DOCUMENTS

| WO | 91/14378 | 10/1991 | ......... C07C/227/00 |
| WO | 95/30689 | 11/1995 | ............ C07K/5/06 |

*Primary Examiner*—Paul J. Killos
*Assistant Examiner*—Mahreen Chaudhry
(74) *Attorney, Agent, or Firm*—Fitzpatrick, Cella, Harper & Scinto; Jeffrey M Hoster

(57) ABSTRACT

The synthesis of N-[N-(3,3-dimethylbutyl)-L-α-aspartyl]-L-phenylalanine 1-methyl ester via conversion under reducing conditions of novel imidazolidinone(s) is disclosed.

23 Claims, No Drawings

METHOD FOR THE PREPARATION OF N-NEOHEXYL-α-ASPARTYL-L-PHENYLALANINE METHYL ESTER FROM IMIDAZOLIDIN-4-ONE INTERMEDIATES

This application claims the benefit of U.S. Provisional Application No. 60/109,132, filed Nov. 19, 1998.

BACKGROUND OF THE INVENTION

1. Field of the Invention

This invention relates to an improved method for the preparation of an N-alkylated aspartame derivative, which is a particularly useful sweetening agent.

2. Related Background Art

N-[N-(3,3-dimethylbutyl)-L-α-aspartyl]-L-phenylalanine 1-methyl ester, or neotame, having the formula below, is a highly intense non-nutritive sweetening agent useful to impart sweetness to a wide variety of food products.

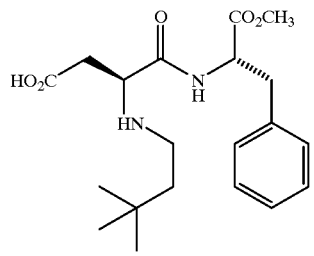

This sweetener, disclosed in U.S. Pat. No. 5,480,668, is approximately 8,000 times as sweet as sucrose, on a weight basis. Thus, very small quantities of this sweetening agent may be used to produce foods and food products that are equi-sweet tasting to presently available high caloric food products.

Several syntheses of neotame using reductive alkylation of aspartame and 3,3-dimethylbutyraldehyde have been reported. U.S. Pat. No. 5,480,668 discloses a method of adding the 3,3-dimethylbutyraldehyde to a mixture of aspartame and reducing agent in methanol. Sodium cyanoborohydride is disclosed as a useful reducing agent. U.S. Pat. No. 5,510,508 discloses a method using hydrogen at 1 bar or less in the presence of a platinum or palladium catalyst as a reducing agent. In this method, a pH 4.5–5 aqueous-alcoholic solution of aspartame and, 3,3-dimethylbutyraldehyde was treated at room temperature with the reducing agent. The product was purified by precipitation and filtration after evaporation of the alcohol from the solution.

U.S. Pat. No. 5,728,862 describes a method comprising treating a solution of aspartame and 3,3-dimethylbutyraldehyde, in an organic solvent with hydrogen in the presence of a catalyst as a reducing agent. After removal of the catalyst, water was added to form an aqueous/organic solvent solution containing about 17% to about 30% of the organic solvent, by weight, from which the neotame was obtained by precipitation and filtration.

In summary, the preparation of neotame by reductive alkylation of aspartame and 3,3-dimethylbutyraldehyde may proceed by addition of a reducing agent to an aspartame/3,3-dimethylbutyraldehyde mixture or addition of 3,3-dimethylbutyraldehyde to an aspartame/reducing agent mixture, typically in methanol or aqueous methanol. Useful reducing agents include hydrogen in the presence of a palladium or platinum catalyst and hydride reducing agents, especially borohydride reducing agents. However, each of these methods is accompanied by the formation of several impurities, as well as recovery of unreacted starting materials. Since sweetening agents are primarily used in foods for human consumption, it is extremely important that such sweetening agents be produced using methods which provide a high purity product.

Accordingly, it would be desirable to develop very efficient and cost-effective methods of preparing high-purity neotame from readily available or readily obtainable materials.

SUMMARY OF THE INVENTION

This invention relates to the synthesis of N-[N-(3,3-dimethylbutyl)-L-α-aspartyl]-L-phenylalanine 1-methyl ester (neotame) via the reduction of a novel imidazolidinone intermediate.

The method of this invention comprises the steps of reducing at least one reactant selected from (i) α-methyl hydrogen-D-2-(2,2-dimethylpropyl)-5-oxo-α-L-(phenylmethyl)-1,4(L)-imidazolidine diacetate (trans imidazolidinone) having the formula:

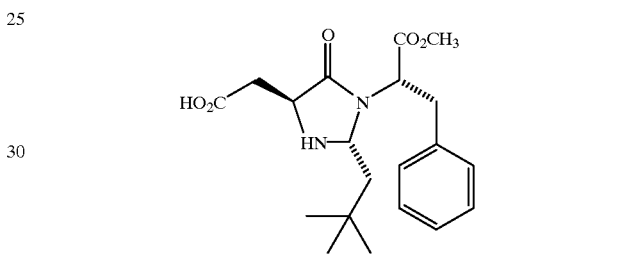

(ii) α-methyl hydrogen-L-2-(2,2-dimethylpropyl)-5-oxo-α-L-(phenylmethyl)-1,4(L)-imidazolidine diacetate (cis imidazolidinone) having the formula:

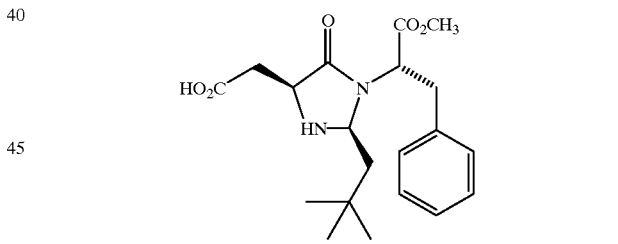

(iii) an imine having the formula:

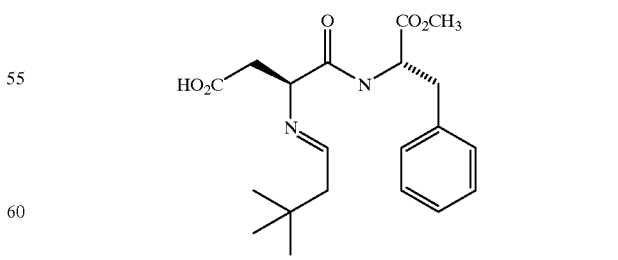

or (iv) mixtures thereof to form N-[N-(3,3-dimethylbutyl)-L-α-aspartyl]-L-phenylalanine 1-methyl ester. In a preferred embodiment of the invention, the imidazolidinone intermediate is formed by the reaction of aspartame and 3,3- dimethylbutyraldehyde. This invention also relates to the novel imidazolidinones used in the method of this invention.

DETAILED DESCRIPTION OF THE INVENTION

Aspartame I reacts with 3,3-dimethylbutyraldehyde (II) to form neotame (III) under reductive alkylation reaction conditions, as illustrated in Scheme I, below.

aldehyde and aspartame on addition of water. Under the reaction conditions specified in the method of this invention, the imine may reversibly cyclize to form a 5-membered imidazolidinone. This imidazolidinone may possess either cis or trans stereochemistry, and undergoes equilibration in solution based on the relative stereochemistry of the 3,3-dimethylbutyryl moiety and the methylene carboxyl moiety at the 2 and 4 positions on the heterocyclic ring. Alternatively, these imidazolidinone isomers may be desig-

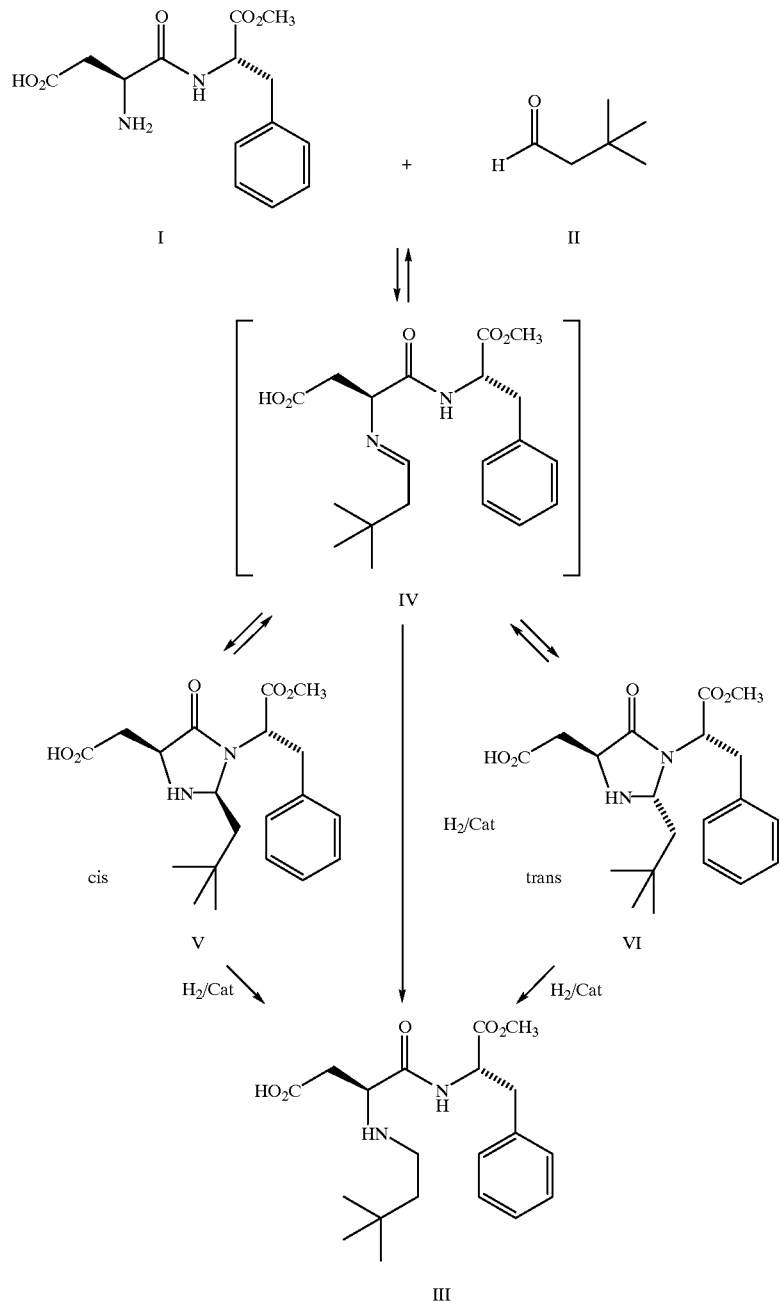

Aspartame (I) and the butyraldehyde (II) reversibly react to form an imine (IV), also called a Schiff's base, and water. This imine is a condensation reaction product of the aldehyde and aspartame, which may convert back to the starting nated as D- and L-isomers, corresponding to the cis and trans isomers, respectively. Cyclization of the imine provides both cis imidazolidinone (V) and trans imidazolidinone (VI).

According to one embodiment of the method of this invention aspartame (I) may be reacted with 3,3-dimethylbutyraldehyde to form a mixture of imine (IV) and imidazolidinones (V and VI) which are in equilibrium with the starting aspartame (I) and butyraldehyde (II). In the absence of water, the equilibrium balance shifts equilibria formation to the imidazolidinone (V and VI); the presence of water shifts equilibria formation to the hydrolysis products/starting materials aspartame (I) and butyraldehyde (II). Formation of imidazolidinone will occur in both the presence or absence of water. However, use of reaction conditions that favor formation of the imidazolidinone by decreasing the water content of the reaction mixture are preferred. For example, use of drying agents or chemical reagents that react with water irreversibly will shift the reaction toward formation of imidazolidinone.

Advantageously, it has been discovered that the imidazolidinone possesses limited solubility in the solvents and solvent mixtures used in the method of this invention. Removal of imidazolidinone by precipitation of the imidazolidinone from the reaction mixture is another way of shifting equilibrium conditions to favor formation of the imidazolidinone. Solid imidazolidinone may be readily isolated from the reaction mixture by filtration, decantation or centrifugation. The solid material produced by the method of this invention may be composed of a mixture of both cis and trans imidazolidinones. The solid imidazolidinone mixture may be used as isolated from the reaction mixture, or may dried.

As indicated above, appropriate selection of the reaction solvent provides for the isolation of solid imidazolidinone by filtration from the reaction mixture. Generally, formation of the imidazolidinone may be conducted in polar protic or polar aprotic solvents. Solvents that are useful for the formation of imidazolidinone according to this invention include $C_1$–$C_4$ alkyl alcohols, tetrahydrofuran, dimethylformamide, dimethylsulfoxide, ethyl acetate and the like, mixtures thereof or aqueous mixtures thereof. Preferably, imidazolidinone formation may be conducted in polar protic or polar aprotic anhydrous solvents. Exemplary preferred solvents include anhydrous $C_1$–$C_4$ alkyl alcohols, tetrahydrofuran, dimethylformamide, dimethylsulfoxide, ethyl acetate and the like, or mixtures thereof. More preferably, imidazolidinone formation may be conducted in anhydrous $C_1$–$C_4$ alkyl alcohol solvents, and most preferably, imidazolidinone formation may be conducted in anhydrous methanol (absolute methanol).

The pH of the reaction mixture for formation of the imidazolidinone mixture is typically between about 4.0 to about 6.0, more preferably, between about 4.5 and 5.5. If desired, the pH of the reaction mixture may be adjusted accordingly.

A preferred manner of obtaining the starting material(s) used in the method of this invention includes condensation of aspartame and 3,3-dimethylbutyraldehyde to form imidazolidinone. This condensation may be conducted by forming a mixture of the aspartame and aldehyde in a selected solvent or solvent mixture. The aspartame and aldehyde may be added to the solvent or solvent mixture in any order. Imidazolidinone formation may be conducted using a molar ratio of aspartame to 3,3-dimethyl butyraldehyde of about 1:0.8 to about 1:1.1. Preferably, imidazolidinone formation may be conducted by combining using a molar ratio of aspartame to 3,3-dimethyl butyraldehyde of about 1:0.98. Optionally, dehydrating agents, such a trimethyl orthoformate, may also be included in the reaction mixture. If desired, the pH of the reaction mixture may be adjusted accordingly. The resulting reaction mixture, which may be heterogeneous, is heated to a temperature of about 20° C. to about 60° C., preferably about 35° C. to about 45° C. for approximately 0.5 to 12 hours, and preferably for 1 to 2 hours. At the end of the reaction, the white solids that have formed are filtered, washed with solvent and dried to provide a solid mixture of cis and trans imidazolidinones (V and VI).

As previously indicated, this invention is directed to a method for the preparation of neotame (III) by treatment of novel imidazolidinone(s) under reducing conditions. According to the method of the invention, the imidazolidinones may be directly converted under reducing conditions to neotame or may undergo ring-opening to re-form imine, which may then be reduced to the neotame. Conversion, under reducing conditions, of each of the cis and trans imidazolidinone isomers forms neotame. Advantageously, conversion of the imidazolidinone mixture, under reducing conditions, forms neotame without generating substantial quantities of di-alkylated impurities. Excess 3,3-dimethylbutyraldehyde present during conventional reductive alkylations leads to formation of di-alkylated aspartame impurities, e.g. di-alkylated aspartame (alkylated neotame), di-alkylated imidazolidinone or di-alkylated aspartame impurities. Specifically, use of 3,3-dimethylbutyraldehyde forms di-neohexyl aspartame or di-neohexyl imidazolidinone impurities. In the method of this invention, any excess 3,3-dimethyl-butyraldehyde that may lead to formation of di-alkylated impurities may be removed from the imidazolidinone solid mixture by filtration and/or drying of the solid mixture. Accordingly, conversion of the imidazolidinone(s) to neotame may be conducted in the substantial absence of butyraldehyde. However, due to the ability of the imine, imidazolidinones and starting materials, i.e., aspartame and butyraldehyde, to inter-convert in presence of water, some equilibrium level concentration of the 3,3-dimethylbutyraldehyde will be present during the catalytic hydrogenation reaction. Thus, while the formation of di-alkylated impurities cannot be eliminated, they may be substantially reduced using the method of this invention.

Di-alkylated imidazolidinone (VII), di-neohexyl imidazolidinone, may be formed by the reaction of neotame (III) and excess 3,3-dimethylbutyraldehyde, according to Scheme II. Advantageously, the reaction is reversible and the di-neohexyl imidazolidinone hydrolyzes in the presence of water to give neotame and 3,3-dimethylbutyraldehyde, which are readily separable. Thus, this di-alkylated imidazolidinone (VII) impurity may be easily removed. Di-alkylated aspartame, or neohexyl-neotame (VIII), may be prepared by reductive alkylation of neotame with 3,3-dimethylbutyraldehyde and is formed as a by-product impurity of the reductive alkylation of aspartame and butyraldehyde. In contrast to the di-alkylated imidazolidinone, the di-alkylated aspartame does not hydrolyze or decompose in water and thus cannot be as readily separated from the desired neotame.

SCHEME II

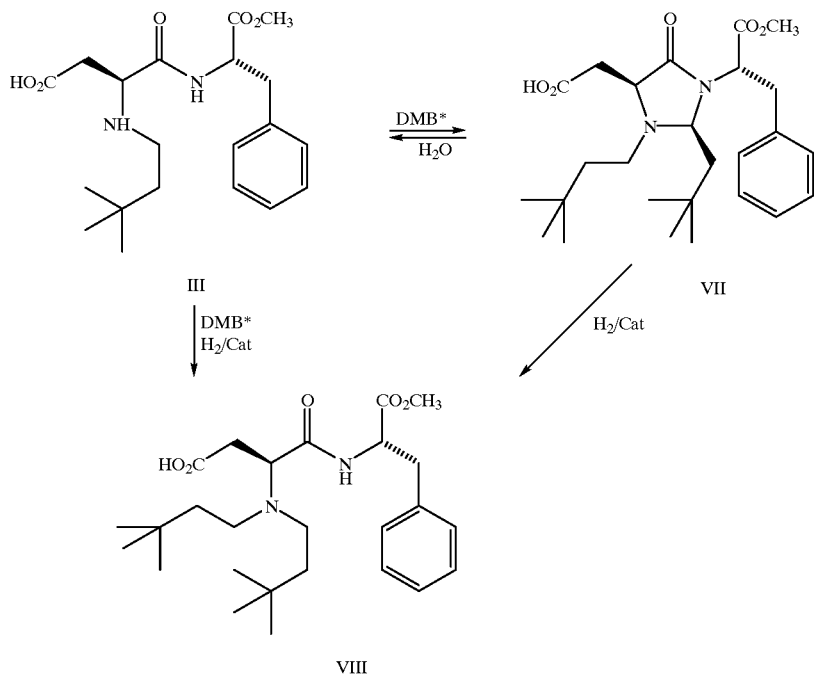

DMB* = 3,3-dimethylbutyraldehyde

Conversion, under reducing conditions, of the imidazolidinone mixture to neotame may be conducted using methods well known to those skilled in the art. For example, reducing conditions, or reducing agents, useful in this invention to convert the imidazolidinone mixture to neotame include catalytic hydrogenation, homogenous catalysis, metal hydride reductions, dissolving metal reductions and other non-metallic reductions, such as reductions effected by hydrazinediimide, silanes, formic acid, photoreductions or enzymatic or microbial reductions, as described by Michael B. Smith, "Organic Synthesis," McGraw-Hill, Inc., New York, N.Y., 1994, the disclosure of which is incorporated by reference herein. Preferably, the conversion, or reductive alkylation, is effected using, for example, catalytic hydrogenation, zinc and hydrochloric acid, sodium cyanoborohydride, sodium acetoxyborohydride, lithium borohydride, sodium borohydride, iridium triphenyl phosphine, borane in pyridine, or formic acid. Most preferably, the imidazolidinone(s) may be reduced by catalytic hydrogenation.

Conversion, under hydrogenation conditions, of the imidazolidinone mixture to neotame is conducted using a hydrogenation catalyst under a hydrogen atmosphere at a pressure and temperature sufficient to effect the conversion. Any hydrogenation catalyst based on platinum or palladium may be used to catalyze the hydrogenation of the imidazolidinone(s) to neotame. Useful hydrogenation catalysts include palladium on activated carbon, platinum on activated carbon, platinum black or palladium black. Other hydrogenation catalysts include, without limitation, nickel on silica, nickel on silica and alumina, Raney nickel, ruthenium black, ruthenium on carbon, palladium oxide, palladium hydroxide on carbon, rhodium black, rhodium on carbon, and rhodium on alumina. Preferably, catalysts based on palladium or platinum are used.

More preferably, catalytic conversion under hydrogenation conditions is conducted using a 5% palladium on carbon catalyst. The catalyst is present in the reaction mixture in an amount effective to produce neotame in acceptable yield from the imidazolidinone(s). Generally, the weight ratio of catalyst to imidazolidinone(s) is about 0.005:1 to about 0.2:1, and most preferably about 0.05:1. The pressure of the hydrogen gas used to effect conversion under hydrogenation conditions of the imidazolidinone(s) may be from atmospheric to about 1000 psig, preferably, from about 15 psig to about 100 psig. More preferably, the reaction is conducted under a hydrogen atmosphere of about 40 psig to about 60 psig.

The catalytic hydrogenation of the imidazolidinone(s) may be conducted in polar protic or polar aprotic solvents. Exemplary solvents include $C_1$–$C_4$ alkyl alcohols, tetrahydrofuran, dimethylformamide, dimethylsulfoxide, ethyl acetate and the like, mixtures thereof or aqueous mixtures thereof. Preferably, the hydrogenation may be conducted in anhydrous polar protic or polar aprotic solvents. Exemplary preferred anhydrous solvents include anhydrous $C_1$–$C_4$ alkyl alcohols, tetrahydrofuran, dimethylformamide, dimethylsulfoxide, ethyl acetate and the like, or mixtures thereof. More preferably, hydrogenation may be conducted in anhydrous $C_1$–$C_4$ alkyl alcohol solvents, and most preferably, hydrogenation may be conducted in anhydrous methanol (absolute methanol).

The catalytic hydrogenation may be conducted by first mixing the imidazolidinone(s) and hydrogenation catalyst in a selected solvent or solvent mixture. The resulting mixture may then be placed under a hydrogen atmosphere of about 15 to about 100 psig and the hydrogenation may be conducted at a temperature of about 20° C. to about 60° C., preferably about 35° C. to about 40° C. for approximately 6 to 48 hours, and preferably for 12 to 16 hours. The resulting solution containing N-[N-(3,3-dimethylbutyl)-L-α-aspartyl]-L-phenylalanine 1-methyl ester can then be filtered to remove the insoluble hydrogenation catalyst. Standard filtration techniques may be used. Preferably, the solution is filtered through a layer of filtering aid, such cellulose or Celite®. After filtration, the volume of solvent or solvent mixture used in the hydrogenation reaction may be reduced by evaporation under reduced pressure followed by crystallization. Advantageously, the recovered hydrogenation catalyst (such as Pd, Pt) may be re-used several times in the reductive alkylation. If other reducing conditions or reducing agents, as described above, are used, the reaction mixture should be treated in a manner consistent with the removal of excess reducing agent and the recovery of the neotame product from the reaction mixture, using conventional techniques.

Purification of the N-[N-(3,3-dimethylbutyl)-L-α-aspartyl]-L-phenylalanine 1-methyl ester may be accomplished by recrystallization or column chromatography. Preferably, the N-[N-(3,3-dimethylbutyl)-L-α-aspartyl-L-phenylalanine 1-methyl ester is purified using the techniques and procedures described in U.S. Pat. Nos. 5,510,508, 5,480,668 5,782,862 and in co-pending application, U.S. patent application Ser. No. 60/110,011, filed Nov. 25, 1998, the disclosures of each of which are incorporated by reference herein.

The preparation of neotame by reductive alkylation of aspartame and 3,3-dimethylbutyraldehyde may proceed without the isolation of imidazolidinone by addition of a reducing agent to an aspartame/3,3-dimethyl-butyraldehyde mixture or addition of 3,3-dimethyl-butyraldehyde to an aspartame/reducing agent mixture at a temperature of about 20° C. to about 60° C., preferably about 35° C. to about 40° C. for approximately 6 to 48 hours, preferably for 12 to 16 hours, wherein the reducing agent may be hydrogen in the presence of a palladium of platinum catalyst and the weight ratio of catalyst to aspartame may be about 0.005:1 to about 0.2:1, preferably about 0.05:1, the pressure of the hydrogen gas may be from atmospheric to about 1000 psig, preferably about 15 psig to about 100 psig, and more preferably, about 40 psig to about 60 psig. The reactants may be added in any order.

The Examples which follow are intended as an illustration of certain preferred embodiments of the invention, and no limitation of the invention is implied.

EXAMPLE 1

Synthesis of Imidazolidinones (α-Methyl hydrogen-D-2-(2,2-dimethylpropyl)-5-oxo-α-L-(phenylmethyl)-1,4(L)-imidazolidine diacetate (VI) and α-Methyl hydrogen-L-2-(2,2-dimethyl-propyl)-5-oxo-α-L-(phenylmethyl)-1,4(L)-imidazolidine diacetate (V)

3,3-Dimethylbutyraldehyde (10 g) was dissolved in 100 mL of anhydrous methanol followed by addition of 10 g of aspartame. The heterogeneous reaction mixture was purged with nitrogen (3 times) and agitated (stirred) under nitrogen at 40° C. for 4 h. At the end of the reaction, the white solids that appeared were filtered and washed with anhydrous methanol (2×30 mL). After drying in a vacuum oven at 35° C. for 16 hrs (vacuum 30 pressure: 25" of Hg°), 6.8 g of a white solid was obtained. Spectral analysis (H&C-NMR, DMSO-d6) and chromatographic analysis (HPLC) indicated that the solid obtained was a mixture of products: 86.5% cis midazolidinone (V), 5.5% trans imidazolidinone (VI) and 8% aspartame (I).

EXAMPLE 2

Synthesis of N-[N-(3,3-dimethylbutyl)-L-α-aspartyl]-L-phenylalanine 1-methyl ester (III) from Imidazolidinones α-Methyl hydrogen-D-2-(2,2 dimethylpropyl)-5-oxo-α-L-(phenylmethyl)-1,4(L)-imidazolidine diacetate (VI) and α-Methyl hydrogen-L-2-(2,2-dimethylpropyl)-5-oxo-α-L-(phenylmethyl)-1,4(L)-imidazolidine diacetate (V)

The solid imidazolidinone mixture (5 g), obtained according to the procedure in Example 1, was charged into a 250 mL Parr bottle, followed by addition of absolute methanol (25 g, 32 mL) and 0.5 g of dry 5% Pd/C (palladium on carbon) catalyst. The reaction vessel was purged first with nitrogen (3 times), then with hydrogen (3 times). The hydrogen pressure in the Parr bottle was set at 40 psi, and the reaction mixture was hydrogenated at 40° C. for 12 hrs. The catalyst was removed by filtration and washed with 2×15 mL of anhydrous methanol. The washings and filtrate were combined and the methanol removed on a rotary evaporator under reduced pressure to provide 4.95 g of crude neotame. Chromatographic analysis (HPLC) indicated that the crude neotame contained: aspartame (2.5% I), neotame (94.1% III), di-neohexyl-aspartame (2% VIII), di-neohexyl imidazolidinone (1.4% VII) (normalized peak areas).

EXAMPLE 3

Synthesis of N-[N-(3,3-dimethylbutyl)-L-α-aspartyl]-L-phenylalanine 1-methyl ester (III) from Imidazolidinones α-Methyl hydrogen-D-2-(2,2-dimethylpropyl)-5-oxo-α-L-(phenylmethyl)-1,4(L)-imidazolidine diacetate (VI) and α-Methyl hydrogen-L-2-(2,2-dimethylpropyl)-5-oxo-α-L-(phenylmethyl)-1,4(L)-imidazolidine diacetate (V)

The solid imidazolidinone mixture (4.5 g), obtained according to the procedure in Example 1, was charged into a 250 mL Parr bottle followed by addition of a solution of methanol and water/1:1 (25 g, 32 mL) and 1.1 g of 5% Pd/C catalyst. The reaction vessel was purged first with nitrogen (3 times), then hydrogen (3 times). The hydrogen pressure in the Parr bottle was set at 40 psi, and the reaction mixture was hydrogenated at 40° C. for 12 hrs. The catalyst was removed by filtration and washed with 2×15 mL of methanol. The washings and filtrate were combined and the methanol removed on a rotary evaporator under reduced pressure to provide 4.3 g of crude neotame. Chromatographic analysis (HPLC) indicated that the crude neotame contained: aspartame (8.4%), neotame (87.5%), di-neohexyl-aspartame (3.2%) and di-neohexyl imidazolidinone (0.9%).

EXAMPLE 4

Synthesis of α-Methyl hydrogen-3-(3,3-dimethyl-butyl)-2-L-(2,2-dimethylpropyl)-5-oxo-α-L-(phenylmethyl)-1,4(L)-imidazolidine diacetate (VII)

Neotame (41.60 g, 0.110 mole) was dissolved in 230 mL of anhydrous methanol. The solution was heated to 40° C. and 3,3-dimethylbutyraldehyde (11.01 g, 0.110 mole) was added. The solution temperature was maintained at 40° C., and stirred for 90 minutes. The methanol was removed under vacuum at 30° C. to provide a yellow oil, that crystallized upon standing. The crude product (20.0 g) was dissolved in 75 mL of methanol, heated to 50° C., then diluted with 50 mL of water, which was added in one portion. The resulting solution was allowed to cool to room temperature to permit crystallization of the di-neohexyl imidazolidinone. The material was filtered and dried at 40° C. under vacuum for 12 hours to give 11.34 g of a off white powder (98.6% pure by HPLC), MP: 132–134° C.,; H$^1$ NMR (400 MHz, CDCl$_3$) δ7.34 (t, 2H, Ar), 7.27 (tt, 1H, Ar), 7.22 (d, 2H, Ar), 3.94 (dd, 1H, C$\underline{H}$), 3.82 (s, 1H, OC$\underline{H}_3$), 3.41–3.55 (m, 6H, C$\underline{H}$, C$\underline{H}_2$), 2.55–2.80 (dd, 2H, C$\underline{H}_2$), 2.16 (m, 2H, C$\underline{H}_2$), 1.53 (m, 2H, C$\underline{H}_2$), 1.27(m, 2H, C$\underline{H}_2$), 0.86 (s, 9H, C$\underline{H}_3$), 0.81 (s, 9H, C$\underline{H}_3$). Anal. Calc'd. for CH$_{26}$H$_{40}$N$_2$O$_5$(460.62): C, 67.80; H, 8.75; N, 6.08. Found: C, 67.47; H, 8.61; N, 6.04.

EXAMPLE 5

Preparation of N-[N-(3,3-dimethylbutyl)-L-α-aspartyl]-L-phenylalanine 1-methyl ester (III) by hydrolysis of α-Methyl hydrogen-3-(3,3-dimethylbutyl)-2-L-(2,2-dimethyl-propyl)-5-oxo-α-L-(phenylmethyl)-1,4(L)-imidazolidine diacetate (VII)

The di-neohexyl imidazolidinone (10 g), obtained according to the method of Example 4, was added to 100 mL of aqueous methanol (75 mL water/25 mL methanol) and the resulting mixture was heated at 35–45° C. for 4–16 hours. Chromatographic analysis (HPLC) of the reaction mixture indicated the exclusive presence (100%) of neotame. No di-neohexyl imidazolidinone was detected.

EXAMPLE 6

Synthesis of N,N-di-(3,3-dimethylbutyl)-L-aspartyl-L-phenylalanine methyl ester (VIII)

Di-neohexyl imidazolidinone (VII, 4 g), obtained according to the method of Example 4, was dissolved in anhydrous methanol (40 mL), followed by addition of 10% Pd/C (400 mg). The mixture was hydrogenated at 40° C. and at hydrogen pressure of 40 psig for 12 hours. The palladium catalyst was removed by filtration through a Celite® bed, which was washed with methanol (2×20 mL). The filtrate and washings were combined and removed under reduced pressure at 40° C. to yield 4 g of crude di-neohexyl aspartame (90% pure by HPLC).

EXAMPLE 7

Synthesis of N,N-di-(3,3-dimethylbutyl)-L-aspartyl-L-phenylalanine methyl ester (VIII) from N-[N-(3,3-dimethylbutyl)-L-α-aspartyl]-L-phenylalanine 1-methyl ester (III)

A mixture of N-(3,3-dimethylbutyl)-L-aspartyl-L-phenylalanine, methyl ester (III) (170 g, 0.449 mole), 3,3-dimethylbutyraldehyde (II) (49.5 g, 0.494 mole) and Pd/C (4%, 25.5 g) in 1.2 L of methanol was hydrogenated (500 psi) at room temperature for 24 hrs. The resulting mixture was filtered through a Celite® pad and washed with methanol (2×500 mL). The filtrate and washings combined and the solvent removed under reduced pressure. The white waxy-like solid was dissolved in diethyl ether (3 L) and washed with water (3×1.5 L). The organic phase was dried over Na$_2$SO$_4$, filtered and evaporated under reduced pressure, to provide crude di-neohexyl aspartame which was purified by several triturations with diethyl ether. Yield 144 g, (70%, >98% pure by HPLC). MP: 111–113° C. FT-IR v$_{max}$, cm$^{-1}$ KBr: 3194, 3032, 2956, 2867, 1736, 1685 (amide I), 1558 (amide II), 1475, 1366, 1271, 744, 700. $^1$H NMR (300 MHz, DMSO-d$_6$) δ: 8.02 (d, 1H, J=15.6), 7.26 (m, 5H), 4.49 (m, 1H), 3.68 (q, 1H, J=5.4), 3.62 (s, 3H), 3.05 (q, 1H), 2.97 (q, 1H), 2.42 (m, 1H), 2.30 (m, 1H), 2.25 (m, 4H), 1.20 (m, 4H), 0.81 (s, 18H). $^{13}$C NMR (75 MHz, DMSO-d$_6$): 176.36 (1C), 172.09 (1C), 172.02 (1C), 137.21 (1C), 129.17 (2C), 128.46 (2C), 126.77 (1C), 60.71 (1C), 53.36 (1C), 51.90 (2C), 46.76 (2C), 41.78 (2C), 36.47 (1C), 31.02 (1C), 29.46 (1C), 29.24 (6C). MS (M+1): 463.4. Anal. Calc. for C$_{26}$H$_{42}$N$_2$O$_5$ (462.63) C, 67.50; H, 9.15; N, 6.06. Found: C, 67.21, 66.97; H, 9.20, 9.12; N, 5.93, 5.90.

EXAMPLE 8

Synthesis of Imidazolidinones (α-Methyl hydrogen-D-2-(2,2-dimethylpropyl)-5-oxo-α-L-(phenylmethyl)-1,4(L)-imidazolidine diacetate (VI) and a-Methyl hydrogen-L-2-(2,2-dimethyl-propyl)-5-oxo-α-L-(phenylmethyl)-1,4(L)-imidazolidine diacetate (V)

Aspartame (40 g) was charged into a 1.0 L Parr shaker followed by a solution of 3,3-dimethylbutyraldehyde (40 g) and methanol (100 mL, HPLC grade). The Parr vessel was sealed and purged with nitrogen (3 times). Under nitrogen, the mixture was agitated at 40° C. for 4 hours. The solids were filtered and washed with 60 mL (3×) of methanol (HPLC grade). The solids were dried under vacuum at 35° C. for approximately 18 hours to provide 33.3 g of a mixture of cis and trans imidazolidinones (>98%, predominantly cis and approximately 2% aspartame by NMR).

EXAMPLE 9

Synthesis of N-[N-(3,3-dimethylbutyl)-L-α-aspartyl]-L-phenylalanine 1-methyl ester (III) from Imidazolidinones α-Methyl hydrogen-D-2-(2,2 dimethylpropyl)-5-oxo-α-L-(phenylmethyl)-1,4(L)-imidazolidine diacetate (VI) and α-Methyl hydrogen-L-2-(2,2-dimethylpropyl)-5-oxo-α-L-(phenylmethyl)-1,4(L)-imidazolidine diacetate (V)

The imidazolidinone mixture (5 g), obtained according to the procedure in Example 8, was charged into a 250 mL Parr bottle followed by addition of dry 5% palladium on carbon (0.5 g) and 25 g of methanol (HPLC grade). The Parr bottle was sealed and purged with nitrogen (3 times) followed by hydrogen (3 times). The hydrogen pressure in the Parr bottle was adjusted to 40 psi and the reaction mixture was hydrogenated at 25° C. for 12 hours. The catalyst was removed by filtration and washed with 15 mL (2×) of methanol (HPLC grade). The filtrate and the washings were combined and the methanol was removed using a rotary evaporator under vacuum. The solids were dried under vacuum at 40° C. overnight to provide 1.7 g of crude neotame. To the dry crude neotame, methanol (3.6 g) and water (8.5 g) were added. The solution was mixed to obtain a homogeneous solution and then stored in the refrigerator overnight for static crystallization. The material was filtered, washed with cold water and dried at 40° C. under vacuum for 20 hours to give 0.7 g (>85% by HPLC) neotame.

EXAMPLE 10

Synthesis of N-[N-(3,3-dimethylbutyl)-L-α-aspartyl]-L-phenylalanine 1-methyl ester (III) from Imidazolidinones α-Methyl hydrogen-D-2-(2,2 dimethylpropyl)-5-oxo-α-L-(phenylmethyl)-1,4(L)-imidazolidine diacetate (VI) and α-Methyl hydrogen-L-2-(2,2-dimethylpropyl)-5-oxo-α-L-(phenylmethyl)-1,4(L)-imidazolidine diacetate (V)

The imidazolidinone mixture (5 g), obtained according to the procedure in Example 8, was charged into a 250 mL Parr bottle followed by addition of dry 5% palladium on carbon (0.5 g) and 25 g of methanol (HPLC grade). The Parr bottle was sealed and purged with nitrogen (3 times) followed by hydrogen (3 times). The hydrogen pressure in the Parr bottle was adjusted to 40 psi and the reaction mixture was hydrogenated at 40° C. for 12 hours. The catalyst was removed by filtration and washed with 15 mL (2x) of methanol (HPLC grade). The filtrate and the washings were combined and the methanol was removed using a rotary evaporator under vacuum. The solids were dried under vacuum at 40° C. overnight to provide 5.7 g of crude neotame. To the dry crude neotame, methanol (17.7 g) and water (41.2 g) were added. The solution was mixed to obtain a homogeneous solution and then stored in the refrigerator overnight for static crystallization. The material was filtered, washed with cold water and dried at 40° C. under vacuum for 20 hours to give 3.2 g (>96% by HPLC) neotame.

EXAMPLE 11

Synthesis of N-[N-(3,3-dimethylbutyl)-L-α-aspartyl]-L-phenylalanine 1-methyl ester (III) from Imidazolidinones α-Methyl hydrogen-D-2-(2,2 dimethylpropyl)-5-oxo-α-L-(phenylmethyl)-1,4(L)-imidazolidine diacetate (VI) and α-Methyl hydrogen-L-2-(2,2-dimethylpropyl)-5-oxo-α-L-(phenylmethyl)-1,4(L)-imidazolidine diacetate (V)

The imidazolidinone mixture (4.5 g), obtained according to the procedure in Example 8, was charged into a 250 mL Parr bottle followed by addition of 5% palladium on carbon (with 61.45% water) (2.85 g) and 25 g of methanol/water (1:1). The Parr bottle was sealed and purged with nitrogen (3 times) followed by hydrogen (3 times). The hydrogen pressure in the Parr bottle was adjusted to 40 psi and the reaction mixture was hydrogenated at 25° C. for 12 hours. The catalyst was removed by filtration and washed with 15 mL (2x) of methanol. The filtrate and the washings were combined and the methanol was removed using a rotary evaporator under vacuum. The solids were dried under vacuum at 40° C. overnight to provide 0.5 g of crude neotame (47.2% aspartame, 29.3% neotame, 5.8% cis imidazolidinone, 4.2% trans imidazolidinone, 1.9% di-neohexyl-aspartame and 1.7% di-neohexyl imidazolidinone).

EXAMPLE 12

Synthesis of N-[N-(3,3-dimethylbutyl)-L-α-aspartyl]-L-phenylalanine 1-methyl ester (III) from Imidazolidinones α-Methyl hydrogen-D-2-(2,2 dimethylpropyl)-5-oxo-α-L-(phenylmethyl)-1,4(L)-imidazolidine diacetate (VI) and α-Methyl hydrogen-L-2-(2,2-dimethylpropyl)-5-oxo-α-L-(phenylmethyl)-1,4(L)-imidazolidine diacetate (V)

The imidazolidinone mixture (4.5 g), obtained according to the procedure in Example 8, was charged into a 250 mL Parr bottle followed by addition of 5% palladium on carbon (with 61.45% water) (2.85 g) and 25 g of methanol/water (1:1). The Parr bottle was sealed and purged with nitrogen (3 times) followed by hydrogen (3 times). The hydrogen pressure in the Parr bottle was adjusted to 40 psi and the reaction mixture was hydrogenated at 40° C. for 12 hours. The catalyst was removed by filtration and washed with 15 mL (2x) of methanol. The filtrate and the washings were combined and the methanol was removed using a rotary evaporator under vacuum. The solids were dried under vacuum at 40° C. overnight to provide 2.1 g of crude neotame. To the dry crude neotame, methanol (6.2 g) and water (14.5 g) were added. The solution was mixed to obtain a homogeneous solution and then stored in the refrigerator overnight for static crystallization. The material was filtered, washed with cold water and dried at 40° C. under vacuum for 20 hours to give 1.1 g (>99% by HPLC) neotame.

EXAMPLE 13

Synthesis of N-[N-(3,3-dimethylbutyl)-L-α-aspartyl]-L-phenylalanine 1-methyl ester (III) from 3,3-Dimethylbutyraldehyde and α-L-Aspartyl-L-phenylalanine 1-methyl ester (Aspartame)

Aspartame (50 g) was charged to a 2.0 L 3-neck glass vessel followed by the addition of 3,3-dimethylbutyraldehyde (17.2 g) and methanol (500 g). The heterogeneous mixture was stirred at 23–25° C. for 7–8 hours. At the end of the 7–8 hours, HPLC analysis of the solids indicated 56.6% aspartame, 32.3% cis-imidazolidinone and 11.1% trans-imidazolidinone. The mother liquor contained 60.6% aspartame, 11.3% cis-imidazolidinone and 28.1% trans-imidazolidinone. The mixture (containing solids and mother liquor) was then charged into a 1.0 L Parr hydrogenator (fitted with a heating coil), with stirring, followed by 5% Pd/C (6.5 g; with 61.45% water). The reaction vessel was purged first with nitrogen (3 times), then with hydrogen (3 times). The hydrogen pressure in the reaction vessel was set at 40 psig and the reaction mixture was hydrogenated at 25° C. for 14 hours. The hydrogen pressure was released and the reaction vessel purged with nitrogen (3 times). The catalyst was removed by filtration and washed with 50 ml (2x) methanol. The washings and filtrate were combined and the methanol removed under reduced pressure. HPLC analysis indicated that the crude neotame contained: (6.7%) aspartame, (1.7%) di-neohexyl aspartame, (2.2%) of a mixture of cis and trans imidazolidinones and (0.9%) of di-neohexyl imidazolidinone. To the crude neotame, methanol (134 g) and water (402 g) were added. The mixture was stirred to obtain solution. The solution was cooled with stirring to 5° C. The crystallized neotame was filtered and dried at 40° C. under vacuum for 20 hours to give 43.1 g (67% yield) of an off white powder (>98% pure by HPLC).

EXAMPLE 14

Synthesis of N-[N-(3,3-dimethylbutyl)-L-α-aspartyl]-L-phenylalanine 1-methyl ester (III) from 3,3-Dimethylbutyraldehyde and α-L-Aspartyl-L-phenylalanine 1-methyl ester (Aspartame)

Aspartame (50 g) was charged to a 2.0 L 3-neck glass vessel followed by the addition of 3,3-dimethylbutyraldehyde (17.2 g) and methanol (500 g). The heterogeneous mixture was stirred at 40° C. for 7 hours. At the end of the 7 hours an HPLC analysis of the solids indicated 43.2% aspartame, 45.7% cis-imidazolidinone and 11.1% trans-imidazolidinone. The mother liquor contained 35.4% aspartame, 29.0% cis-imidazolidinone and 35.6% trans-imidazolidinone. The mixture (containing solids and mother liquor) was then charged into a 1.0 L Parr hydrogenator (fitted with a heating coil), with stirring, followed by 5% Pd/C (6.5 g with 61.45% water). The reaction vessel was purged first with nitrogen (3 times), then with hydrogen (3 times). The hydrogen pressure in the reaction vessel was set at 40 psig and the reaction mixture was hydrogenated at 40° C. for 14 hours. The hydrogen pressure was released and the reaction vessel purged with nitrogen (3 times). The catalyst was removed by filtration and washed with 50 ml (2x) methanol. The washings and filtrate were combined and the methanol removed under reduced pressure. HPLC analysis indicated that the crude neotame contained: (3.6%) aspartame, (2.1%) di-neohexyl aspartame, (0.0%) of cis and trans imidazolidinone and (0.8%) of di-neohexyl imidazolidinone. To the crude neotame, methanol (172 g) and water (515 g) were added. The mixture was stirred to obtain solution. The solution was cooled with stirring to 5° C. The crystallized neotame was filtered and dried at 40° C. under vacuum for 20 hours to give 41.9 g (65% yield) of an off white powder (>96% pure by HPLC).

Other variations or modifications, which will be obvious to those skilled in the art, are within the scope and teachings of this invention. This invention is not to be limited except as set forth in the following claims.

We claim:

1. A method for preparing N-[N-(3,3-dimethylbutyl)-L-α-aspartyl]-L-phenylalanine 1-methyl ester of the formula

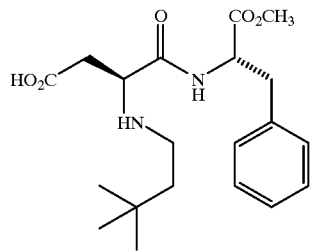

comprising the step of reducing in a solvent at least one reactant selected from (i) a trans imidazolidinone having the formula:

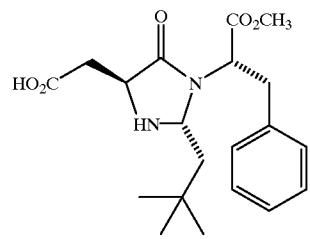

(ii) a cis imidazolidinone having the formula:

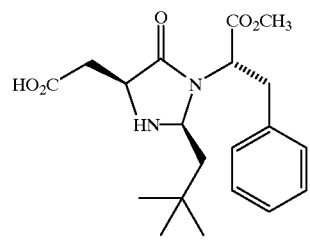

(iii) an imine having the formula:

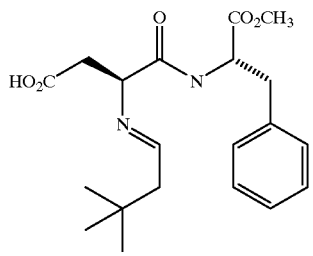

or (iv) mixtures thereof to form N-[N-(3,3-dimethylbutyl)-L-a-aspartyl]-L-phenylalanine methyl ester.

2. The method according to claim 1, wherein the solvent is selected from the group consisting of a $C_1$–$C_4$ alkyl alcohol, tetrahydrofuran, dimethylformamide, dimethylsulfoxide, ethyl acetate, mixtures thereof and aqueous mixtures thereof.

3. The method according to claim 2, wherein the solvent is an anhydrous solvent.

4. The method according to claim 3, wherein the solvent is anhydrous methanol.

5. The method according to claim 1, wherein said reactant is an imidazolidinone mixture comprising (i) the trans imidazolidinone and (ii) the cis imidazolidinone or (i) the trans imidazolidinone, (ii) the cis imidazolidinone and (iii) the imine.

6. The method according to claim 5, further comprising the step of reacting aspartame with 3,3-dimethylbutyraldehyde in a reaction solvent to form the imidazolidinone mixture.

7. The method according to claim 6, wherein a mixture of aspartame and 3,3-dimethylbutyraldehyde in said reaction solvent has a pH of about 4.5 to about 5.5.

8. The method according to claim 6, where the molar ratio of aspartame to 3,3-dimethyl butyraldehyde is about 1:0.8 to about 1:1.1.

9. The method according to claim 6, where the molar ratio of aspartame to 3,3-dimethyl butyraldehyde is about 1:0.98.

10. The method according to claim 6, further comprising the step of isolating said imidazolidinone mixture prior to the step of conversion under hydrogenation conditions.

11. The method according to claim 6, wherein the reaction solvent is selected from the group consisting of a $C_1$–$C_4$ alkyl alcohol, tetrahydrofuran, dimethylformamide, dimethylsulfoxide, ethyl acetate, mixtures thereof and aqueous mixtures thereof.

12. The method according to claim 11, wherein the reaction solvent is an anhydrous solvent.

13. The method according to claim 6, wherein the reaction solvent is anhydrous methanol.

14. The method according to claim 1, wherein the step of reducing is by catalytic hydrogenation.

15. The method according to claim 14, wherein catalytic hydrogenation comprises treating the reactant with hydrogen in the presence of a hydrogenation catalyst.

16. The method according to claim 15, wherein the hydrogenation catalyst is a palladium, platinum, rhodium, nickel, rutheninm or iridium based catalyst.

17. The method according to claim 15, wherein the hydrogenation catalyst is a palladium or platinum based catalyst.

18. The method according to claim 15, wherein the hydrogenation catalyst is a palladium on carbon.

19. The method according to claim 15, wherein the weight ratio of hydrogenation catalyst to reactant is in a range of about 0.005:1 to about 0.2:1.

20. The method according to claim 15, wherein the pressure of hydrogen is between about atmospheric and about 1000 psi.

21. The method according to claim 15, wherein the temperature is about 20° C. to about 60° C.

22. The method according to claim 1, wherein the N-[N-(3,3-dimethylbutyl)-L-α-aspartyl]-L-phenylalanine 1-methyl ester is recovered by crystallization from the solvent.

23. The method according to claim 1, wherein the N-[N-(3,3-dimethylbutyl)-L-α-aspartyl]-L-phenylalanine 1-methyl ester is recovered by evaporation of the solvent.

* * * * *